(12) United States Patent
Kriksunov et al.

(10) Patent No.: US 8,029,985 B2
(45) Date of Patent: Oct. 4, 2011

(54) AMPLIFIED BIOASSAY

(75) Inventors: Leo B Kriksunov, Ithaca, NY (US); Geoffrey Wheelock, Ithaca, NY (US); Lee A Henderson, Ithaca, NY (US)

(73) Assignee: Vybion, Inc., Ithaca, NY (US)

( * ) Notice: Subject to any disclaimer, the term of this patent is extended or adjusted under 35 U.S.C. 154(b) by 848 days.

(21) Appl. No.: 11/162,142

(22) Filed: Aug. 30, 2005

(65) Prior Publication Data

US 2006/0046260 A1    Mar. 2, 2006

Related U.S. Application Data

(60) Provisional application No. 60/606,446, filed on Sep. 1, 2004.

(51) Int. Cl.
| C12Q 1/68 | (2006.01) |
| G01N 33/53 | (2006.01) |
| C12P 19/34 | (2006.01) |
| C12N 15/88 | (2006.01) |
| A61K 51/00 | (2006.01) |

(52) U.S. Cl. ........... 435/6; 435/7.1; 435/91.1; 435/91.2; 435/458; 424/1.29

(58) Field of Classification Search .............. 435/6, 7.1, 435/91.1, 183, 458; 436/94, 501; 536/23.1, 536/24.3, 24.33, 25.3, 25.32; 530/300, 350; 424/94.1, 130.1, 178.1, 184.1, 450, 1.29
See application file for complete search history.

(56) References Cited

U.S. PATENT DOCUMENTS

| 3,887,698 A | 6/1975 | McConnell |
| 4,193,983 A | 3/1980 | Ullman |
| 4,241,046 A | 12/1980 | Papahadjopoulos |
| 4,342,826 A | 8/1982 | Cole |
| 4,342,828 A | 8/1982 | Takaku |
| 4,372,745 A | 2/1983 | Mandle |
| 4,522,803 A | 6/1985 | Lenk |
| 4,539,376 A | 9/1985 | Goel |
| 5,389,523 A | 2/1995 | Plant |
| 5,753,519 A | 5/1998 | Durst |
| 5,756,362 A | 5/1998 | Durst |
| 5,789,154 A | 8/1998 | Durst |
| 5,958,791 A | 9/1999 | Roberts |
| 6,086,748 A | 7/2000 | Durst |
| 6,159,745 A | 12/2000 | Roberts |
| 6,248,596 B1 | 6/2001 | Durst |
| 6,358,752 B1 | 3/2002 | Durst et al. |
| 6,576,460 B1 | 6/2003 | Baeumner et al. |
| 6,815,209 B2 | 11/2004 | Baeummer et al. |
| 7,419,796 B2 | 9/2008 | Durst et al. |
| 7,582,430 B2 * | 9/2009 | O'Leary et al. ................ 435/6 |
| 2003/0013091 A1 | 1/2003 | Dimitrov |

(Continued)

OTHER PUBLICATIONS

Brent, R. and Burbulis, I., "Lamp for tadpoles." Nature Methods 2(9):635-6, 2005.

(Continued)

*Primary Examiner* — Frank W Lu

(74) *Attorney, Agent, or Firm* — LeClairRyan

(57) ABSTRACT

A method for assaying a biological sample includes forming sensitized microcapsules filled with unique oligomarkers, capturing sensitized microcapsules in the presence of analytes, releasing oligomarkers from microcapsules and detecting and measuring oligomarkers to detect and quantify presence of analyte in biological sample. Using encapsulated oligomarkers provides for an amplified high sensitivity assay and using plurality of oligomarker types provides for a multiplexed assay.

17 Claims, 10 Drawing Sheets

U.S. PATENT DOCUMENTS

2004/0009944 A1   1/2004   Tam
2004/0072231 A1   4/2004   Mirkin
2004/0110220 A1   6/2004   Mirkin

OTHER PUBLICATIONS

Evanko, D., "Hybridization chain reaction." Nature Methods 1(3):186-7, 2004.

Terry, M., "Partners in Preparedness Against Disease Weapons." Bioterrorism, Drug Discovery and Development pp. 69-74, Aug. 2004.

Valigra, L., "Biosensors Set to Improve Development in Real Time." Cell-Based Technologies, Drug Discovery and Development pp. 58-66, Aug. 2004.

Jamil, H. et al., "Liposomes: The Next Generation." Modern Drug Discovery pp. 37-39, Jan. 2004.

Randerson, J., "Liquid crystals spill beans on anthrax." New Scientist (2451) 22 (Jun. 12, 2004).

"A clever trap nets an array of information." Nature Methods X(X):6-7, 2004.

"Lipospheres in Drug Targets and Delivery: Approaches, Methods, and Applications." CRC Press, Claudio Nastruzzi ed., Catalog p. 1692, Nov. 2004.

Willis, R. C., "Good things in small packages: Nanotech advances are producing mega-results in drug delivery." Modern Drug Discovery pp. 30-36, Jul. 2004.

\* cited by examiner

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial
<220> FEATURE:
<223> OTHER INFORMATION: Oligomarkers

<400> SEQUENCE: 1
ctctctctct ctctctctct                                            20
```

```
<210> SEQ ID NO 2
<211> LENGTH: 20
<212> TYPE: DNA
<213> ORGANISM: Artificial
<220> FEATURE:
<223> OTHER INFORMATION: Oligomarkers

<400> SEQUENCE: 2
tttttttttt tttttttttt                                              20
```

AMPLIFIED BIOASSAY

CROSS-REFERENCE

This application is based upon and claims the benefit under 35 U.S.C. §119 and all applicable foreign and international law of the following U.S. provisional patent application, which is hereby incorporated by reference in its entirety for all purposes: Ser. No. 60/606,446, filed Sep. 1, 2004.

FIELD OF THE INVENTION

The present invention relates to a method for detecting one or more analytes such as determining the presence and/or concentration of antigens, antibodies, polynucleic acids, and like agents in biological fluids. More particularly, the invention relates to a multiplexing amplified bioassay.

BACKGROUND OF THE INVENTION

There is an increasing need for rapid, reliable, inexpensive "in the field" methods for detecting and measuring pathogens and biomarkers in living organisms as well as pollutants and contaminants in the environment and in food sources. Immunoassays comprise one category of specific binding bioassays, which generally rely on the affinity of naturally occurring receptors or antibodies for specific compounds. The specific binding pairs employed in immunoassays are either an antigen or a hapten, and the antibody produced in immune response to the antigen or hapten. Another type of bioassay relies on hybridization binding reaction between complementary single strands of DNA or RNA.

Bioassays are of great importance because of their specificity toward analytes present in complex mixtures, and their high sensitivity. Most bioassays involve the use of a fluorescent, chemiluminescent, electrochemiluminescent, enzyme, electrochemical, or radioactive tag on an immunoreactive species which serves as an indicator that an immunospecific reaction has occurred.

Applying a different classification, immunoassays can be divided into two broad categories of non-amplified assays and amplified assays. Non-amplified assays most often involve the use of a tag, such as fluorescent tag, chemical species tag, electrochemical tag, radioactive label, or the like on an immunoreactive species which serves as an indicator that an immunospecific reaction has occurred. Only one tag per occurrence of immunospecific binding is being activated or released for subsequent detection by optical, chemical, or electrochemical means or by detection of radiation. One of the main disadvantages of the non-amplified assays is low sensitivity of assays.

Amplified assays involve amplification of each binding act between the analyte and the immunoreagent. For example, enzyme-linked immunosorbant assays (ELISAs) involve the use of an enzyme covalently coupled to an immunoreactive reagent to serve as an indicator that an immunospecific reaction has occurred. The enzyme is linked to a secondary reagent, which is added to the assay after the initial immunochemical interaction between the analyte and the immunospecific group, such as an antibody. The enzyme is capable of catalyzing a number of concurrencies of color-changing reaction, generating several hundred turnover events of such reaction in a reasonable period of time. The sensitivity of ELISA is due to the number of turnover events the enzyme is capable of during an incubation period with a substrate that is cleaved to a colored product. While ELISA can be extremely sensitive, it is frequently a very time-consuming assay which is difficult to use in the field.

Another type of an amplified assay is electrochemiluminescence (ECL) based assay, where an electrochemical tag is covalently coupled to an immunoreactive reagent and reacts electrochemically to emit light signal to serve as an indicator that an immunospecific reaction has occurred. Yet another type of an amplified assay is an assay based on method of immunoanalysis which combines immobilized immunochemistry with the technique of flow injection analysis, and employs microscopic spherical microcapsules or sacs, such as animal erythrocytes, polymer microcapsules, liposomes, or similar structures as carriers of detectable reagents. For example, liposomes, or lipid vesicles, can be modified on their surface with analytical reagents, and carry in their internal volume a large number of fluorescent or electroactive tags. After the immunospecific reaction has occurred, the liposomes are disrupted or lysed by the contact with the liposome lysing agent and release a large amount of tags per each binding act. The presence of tags is then detected by chemical, optical, or electrochemical means.

Liposomes have previously been reported as useful components for amplified immunoassays. For example, McConnell et al., U.S. Pat. No. 3,887,698, describe the use of liposomes containing stable free radicals in an electron paramagnetic resonance monitored immunoassay. Mandle et al., U.S. Pat. No. 4,372,745, describe the use of liposomes as fluorescer containing microcapsules, useful in an immunoassay. This assay requires the use of a detergent such as, Triton X-100 to break the liposomes and release the fluorescent compound. Liposomes have also been employed as a tags carrier in an immunoassay described by Ullman et al., U.S. Pat. No. 4,193,983. Tags used in this assay included fluorescers, enzymes and chemiluminescent compounds.

Cole, U.S. Pat. No. 4,342,826, describes an immunoassay method which utilizes antigen-marked, enzyme-encapsulated liposomes which are immunospecifically ruptured in the presence of the cognate antibody and an active complement. The assay utilizes the homogeneous phase reaction between the antibody and complement to release the enzyme tag. U.S. Pat. Nos. 6,248,596; 6,159,745; 6,086,748; 5,958,791; 5,789,154; 5,756,362; 5,753,519; and 5,389,523; by Durst and co-authors, further developed Liposome-enhanced amplified immunoassays and test devices for implementation of these assays. The technology described by Durst et al. has a limited multiplexing potential.

The disadvantages of both ECL and Liposome-based assays is the possibility to detect only one type of pathogen or environmental contaminant in each sample. The simultaneous detection of many pathogens or contaminants in a multiplexing assay format is difficult as only very limited number of uniquely detectable amplification tags compatible with the detection means are available. Typically only one tag is available, such as specific fluorescent, electrochemical, chemical, or radioactive tag.

At the same time, ELISA assays can detect multiple pathogens or environmental contaminants on a specially prepared multiplexing plates, but ELISA is a very time-consuming assay which is difficult to use in the field.

US Patent Application 20040009944 by Tam et al. describes methylated oligonucleotides made immunostimulatory in vivo, by encapsulation of the nucleic acid in a lipid particle. This technology applies to drug development.

US Patent applications 20040110220 and 20040072231 by Mirkin et al. describe using custom oligonucleotides for multiplexing assays employing gold nanoparticles with attached oligonucleotides, which are later released and detected. Conjugating oligonucleotides to particles is a complicated process. There are limitations in the amount and size of oligonucleotides which can be conjugated to gold particles.

US Patent application 20030013091 by Dimitrov describes capturing a target pathogen with a long piece of single strand complementary DNA which has many repeating short oligonucleotide sequences. After that Dimitrov proposes to add fluorescent labels attached to complementary short oligonucleotide sequences. The labels hybridize to the long piece of DNA and thus create amplification. This technology has limited amplification potential. Multiplexing is also complicated as discerning many fluorescent labels from each other is necessary.

In many applications, there is a need to perform multiplexing assays for many pathogens, biomarkers, and/or environmental contaminants simultaneously, due to time constraints and limited amount of analyte sample available. The optimal assay system should be fast, reliable, highly sensitive, and quantitative.

BRIEF DESCRIPTION OF THE INVENTION

In order to aid in the understanding of the present invention, the following terms as used herein and in the claims have the following meanings:

Analyte—the compound or composition to be measured, which may be DNA or RNA molecule, antigen, hapten, or antibody. For example, in a preferred embodiment, the analyte may be either an antigen or an antibody.

Tag—any functional group of a compound capable of ready detection, including chemiluminescent species, electrochemiluminescent groups, colorogenic agents, dyes, fluorogenic agents, and electrochemically active species. Typical tag compounds are fluorescent dyes. These compounds include water soluble derivatives of fluorescein such as carboxyfluorescein and calcein.

Receptor—any compound or composition capable of specifically recognizing and binding another molecule. Natural receptors include immunospecific compounds, such as antibodies, antigens, enzymes, lectins, and the like, as well as complementary single stranded DNA or RNA molecules. For example, in a preferred embodiment, the receptor for an antigen is an antibody, while the receptor for an antibody is either an anti-antibody or, preferably, that antibody's cognate antigen.

Oligonucleotide markers, or oligomarkers—short chains of single stranded DNA or RNA, ranging from about 5 to about 100 oligonucleotides, preferably from about 10 to about 30 oligonucleotides. Oligomarkers can also include a tag which is conjugated to the oligonucleotide molecule.

Sensitized microcapsules—microscopic sac-like structures or microcapsules, having an interior volume defined by a membrane, capable of carrying a large number of oligomarkers, and sensitized with a linked or conjugated receptor on their surface to specific analytes, such as antigens, proteins, DNA fragments, and the like. Sensitized microcapsules are capable of binding to analyte.

The present invention provides an amplified immunoassay or DNA assay which combines immunocapture or hybridization-based capture with the technique of flow injection analysis and employs microscopic sac-like structures, or microcapsules, such as animal erythrocytes, polymer microcapsules, liposomes, and the like, to carry a large number of unique oligonucleotide markers. Said specific markers are released after the immunospecific reaction or hybridization reaction has occurred. The specific oligomarkers are then captured by complementary oligonucleotide targets for quantification of the analyte.

The microcapsules are modified on their surface with receptors (sensitization), and carry in their internal volume unique oligomarkers. After the immunospecific reaction or hybridization reaction has occurred, the microcapsules are disrupted, open, or lysed by contact with the chemical agent, changes in media environment, such as pH or addition of surfactant, or physical effects, including electric impulse, heat, and the like, and release a large amount of oligomarkers per each binding act. The presence of markers is then detected by binding or hybridizing to complementary oligonucleotide molecules situated spatially apart from each other on an inert substrate.

A very large number of unique oligomarkers can be created by varying sequences of oligonucleotides, thus enabling multiplexing of the present assay. A large number of sensitized microcapsules specific to various analytes can be created, each type of specific sensitized microcapsule containing unique oligomarkers. The oligomarkers are molecules comprising a fragment of single strand DNA or RNA with a unique sequence. In another embodiment, the oligomarker is formed from a fragment of single strand DNA and a tag attached to it.

This invention further provides for amplified multiplexing assay capable of simultaneous detection and quantification of more than one pathogen, biomarker, or contaminant. The invention further provides for amplified multiplexing assay for detection, analysis, and quantification of biologically important species, particles, cells, molecules, and functional groups in biological fluids, in the environment, on solid surfaces including tissue samples, and in experimental environments performing drug discovery research.

The invention further improves the amplified bioassays by using primary microcapsules encapsulating oligomarkers and secondary microcapsules encapsulating oligomarkers with tags or tags alone for detecting and amplifying the markers released by primary microcapsules.

DETAILED DESCRIPTION OF THE INVENTION

The assay of the present invention will be illustrated by referring to the assay for one particular entity, e.g. an antigen. The general principles and techniques described herein for assaying an antigen can then be applied to assay for other species such as, for instance antibodies, haptens, DNA, RNA, etc.

Figure 1:
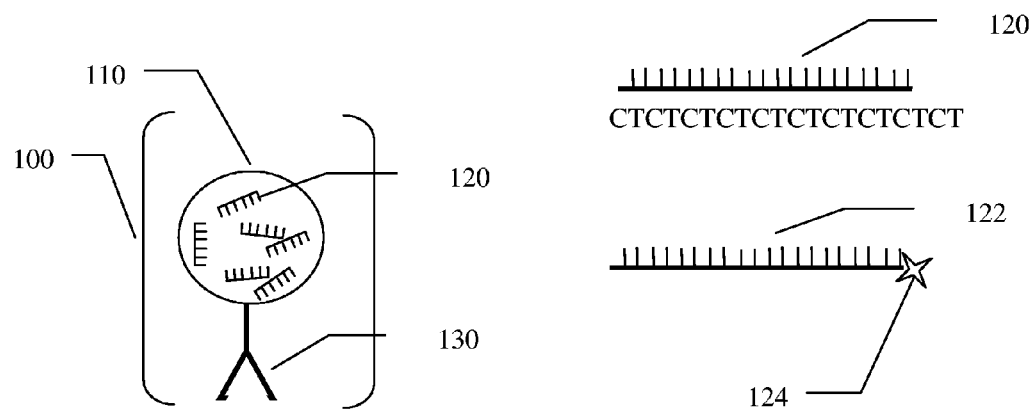
FIG. 1 illustrates the structure of sensitized microcapsules and the structure of oligomarkers (including SEQ ID NO: 1) according to present invention.

Referring now to FIG. 1, the present invention employs microscopic sac-like structures or microcapsules 110, such as animal erythrocytes, polymer microcapsules, liposomes, and the like, to carry a large number of unique oligomarkers 120.

Oligomarkers 120 shown in FIG. 1 are short chains of single stranded DNA or RNA. For illustration, the oligomarker 120 is shown in FIG. 1 as a 20-mer oligonucleotide comprising of twenty nucleotides CTCTCTCTCTCTCTCTCTCT (SEQ ID NO: 1). The oligomarkers according to present invention are ranging from about 5 to about 100 oligonucleotides, preferably from about 10 to about 30 oligonucleotides.

Another embodiment of the oligomarker 122 shown in FIG. 1 includes functional group or tag 124 conjugated to the oligonucleotide molecule. The functional group represents a detectable tag and provides additional means for detecting and quantifying oligomarkers. This tag group is suitable for detection by electrochemical, optical, or other analytical means. The preferred types of the tag 124 is a fluorescent group or a quantum dot. Methods of conjugating tags to oligomarkers are known to these skilled in the art.

The microcapsules 110 are further sensitized to specific analytes, such as antigens, proteins, DNA fragments, and the like, by providing a receptor 130, such as an immunospecific group, for instance, antibody, which is linked or conjugated to the microcapsule 110. The receptor is capable of specifically binding to analyte of interest.

In summary, the sensitized microcapsule 100 shown in FIG. 1 comprises microcapsule 110, filled with unique oligomarkers 120, and sensitized with at least one receptor 130.

In a preferred embodiment, liposomes are utilized as the microcapsules 110. Liposomes are microscopic vesicles composed of closed lipid bilayers. Due to their relatively simple composition and their flexibility for chemical, physical and immunological manipulations, liposomes are readily adapted for encapsulating a range of different markers or tags. Forming microcapsules such as liposomes, encapsulating tags or markers therein, and sensitizing liposomes to bind with a specific analyte, such as antigen, is known and described in the art, for example in US patents by Durst and co-authors cited above. These patents are incorporated herein by reference.

The lipid vesicles or liposomes may be prepared from a wide variety of lipids, including phospholipids, glycol lipids, and as representative examples there may be mentioned lecithin, spingomyelin, dipalmitoyl lecithin, distearoylphosphatidylcholine, etc. The amphiphilic lipids employed for producing liposomes generally have a hydrophilic group, such as a phosphato, carboxylic, sulfato, or amino group, and a hydrophobic group, such as saturated and unsaturated aliphatic hydrocarbons, and aliphatic hydrocarbon groups substituted by one or more aromatic or cycloaliphatic groups. The wall forming compounds for producing the liposomes may further include a steroid component such as cholesterol, cholestanol, and the like. The compounds for producing liposomes are generally known in the art, and no further details in this respect are deemed necessary for a complete understanding of the present invention.

The liposomes may be produced by procedures generally available in the art. For example, liposomes may be produced by a reverse phase evaporation technique wherein the compound or compounds used in producing liposomes are initially dissolved in an organic phase, followed by addition of an aqueous phase and forming of a homogeneous emulsion. After forming the emulsion, the organic solvent is evaporated to form a gel like material, and such gel may be converted to a liposome by agitation or dispersion in an aqueous media.

Procedures for producing liposomes are described, for example, in U.S. Pat. No. 4,241,046 and U.S. Pat. No. 4,342,828.

If a material is to be encapsulated in the liposome, such material may be encapsulated in the liposome by including the material in the aqueous solution in which the liposome is formed. Alternatively, the material may be encapsulated into a previously formed empty liposome (without material to be encapsulated) by the procedure described in U.S. Pat. No. 4,539,376. The liposomes may also be produced by the procedures disclosed in U.S. Pat. No. 4,522,803.

Other types of microcapsules besides liposomes can be utilized, including microcapsules made of polymer materials, biological materials, silicon and silicon compounds, as known in the art.

Figure 2:
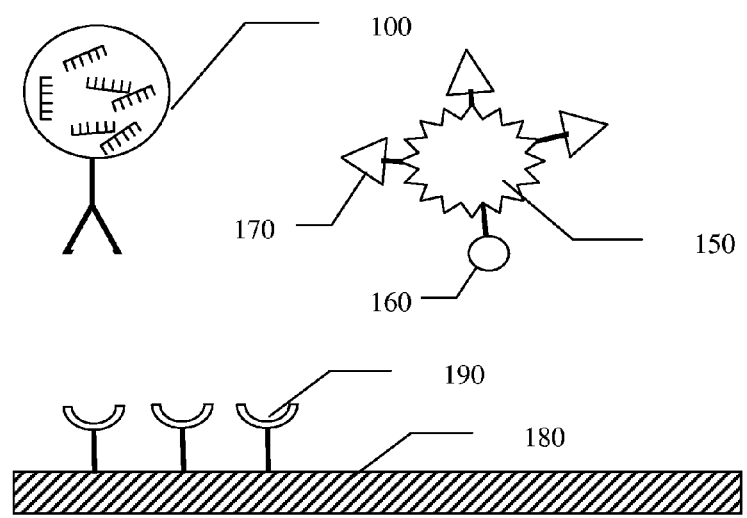
FIG. 2 illustrates the first step of the assay according to present invention, wherein the sensitized microcapsules are bought into contact with the analyte and immobilized receptors.

Referring now to FIG. 2, the first step of the assay according to the present invention is illustrated. The sensitized microcapsule 100 containing oligomarkers is brought into a contact with liquid sample containing analyte 150. The moving of sensitized microcapsules is done in a moving carrier stream, such as aqueous buffer solution. The analyte 150 is characterized by one or more immunospecific groups or receptors shown as 160 and 170. In addition, capture immunospecific groups or receptors 190 specific to the analyte are immobilized on the surface 180, which is a reaction enclosure, a channel in a microfluidic device, an inert particle, magnetic bead, or an assay plate.

Immobilizing receptor groups 190 such as antibodies, on inert solid surfaces, may be accomplished using any technique available to the skilled artisan as known and described in the art. Such techniques include, but are not limited to, adsorption, absorption, ionic bonds, covalent bonds, hydrogen bonds, and the like. Typically, glass and water insoluble polymers are used as the support for the receptor. The support may be in any shape or form. For example, flat objects such as glass slides, polymeric disks or strips, the walls of a test tube, or widely available beads can be employed as the support herein. The bonds between the receptor and the support should be strong enough so that normal washing procedures, or contact with aqueous solutions, including a test serum, do not destroy the attachment means.

One suitable form of chemical binding is to provide bridges of covalent character between the solid support and the receptor. For this purpose the solid support is selected so that it contains or can be provided with suitable reactive functional groups, for example, amino groups, hydroxyl groups, and carboxyl groups, to enable the receptor to be easily bound to the solid support. Especially useful are bridges between the solid support and the receptor having chemical bonds of a covalent nature.

The particular bridge between the receptor and the support is not a critical part of the assay of this invention. The bridge may be of any type, or a mixture of types, as its only purpose is to prevent the receptor from being washed away from the support. One of preferred immobilization methods involves binding biotinylated receptor groups to a support through streptavidin.

Figure 3:
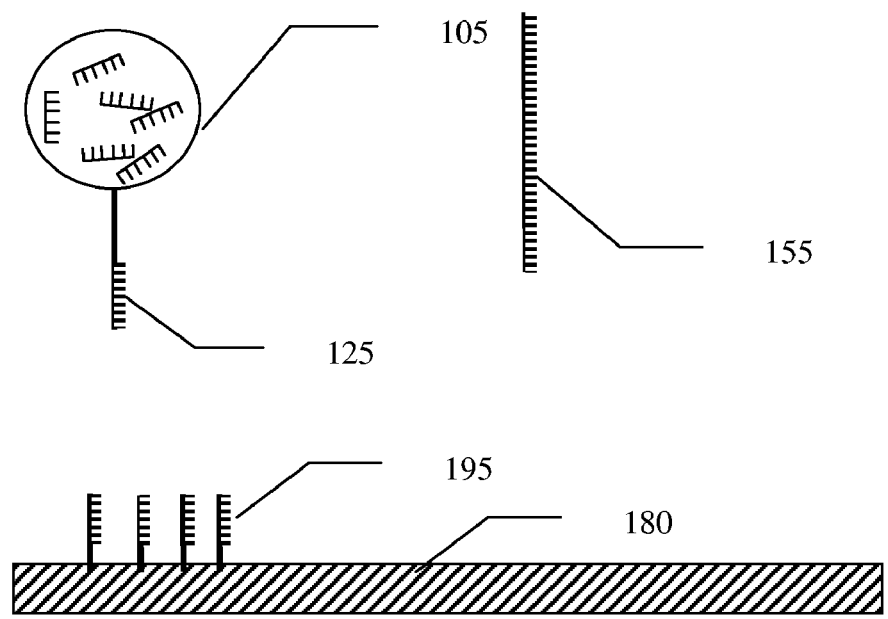
FIG. 3 illustrates embodiment for the first step of the assay according to present invention, wherein the sensitized microcapsules are bought into contact with the analyte and immobilized receptors.

Referring now to FIG. 3, another embodiment of the present invention is illustrated. The analyte 155 is single strand DNA or RNA. The microcapsule 105 containing oligomarkers is sensitized with a DNA or RNA fragment 125 complementary to analyte 155. Capture DNA or RNA fragments 195, complementary to the analyte, are immobilized on the surface 180. In one embodiment, biotinylated capture DNA is bound to the surface through streptavidin.

Both embodiments illustrated in FIGS. 2 and 3 can be employed in the present invention interchangeably, utilizing immunospecific groups (antigens, antibodies, proteins, and the like) or single strand DNA or RNA groups for sensitization of the microcapsules as well as utilizing immunospecific groups (antigens, antibodies, proteins, and the like) or DNA or RNA groups for surface immobilized capture groups within the framework of the present invention.

Figure 4:
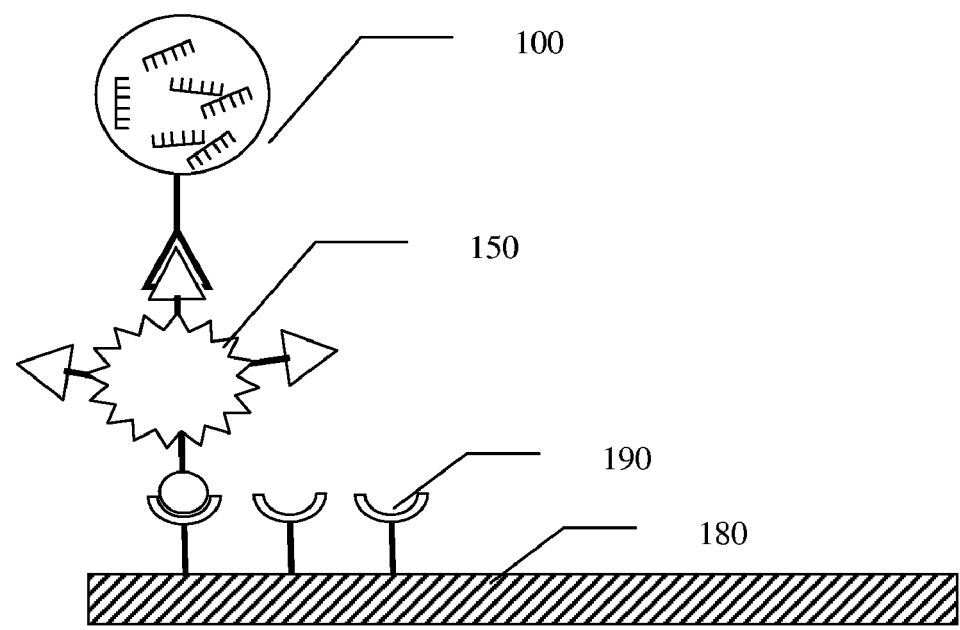
FIG. 4 illustrates capturing of the analyte by the sensitized microcapsules and immobilized receptors.

Referring now to FIG. 4, we illustrate the next step of the present assay, after the sensitized microcapsule 100, containing oligomarkers, was brought into a contact with analyte 150 and the surface immobilized receptors. The analyte 150 is captured by the surface immobilized receptors and is also captured by the sensitized microcapsule 100. In one embodiment of this invention, this capture step is performed sequentially, with the analyte first being captured by the surface immobilized receptors, and the sensitized microcapsule conjugating to the analyte thereafter. In another embodiment, the sensitized microcapsule is first conjugated to the analyte, and then the analyte, bound to the sensitized microcapsule, is captured by the surface immobilized receptors. In yet another embodiment of this invention, both capture steps are performed at the same time, whereas the analyte is brought into contact with both sensitized microcapsules and surface immobilized receptors simultaneously.

Figure 5:
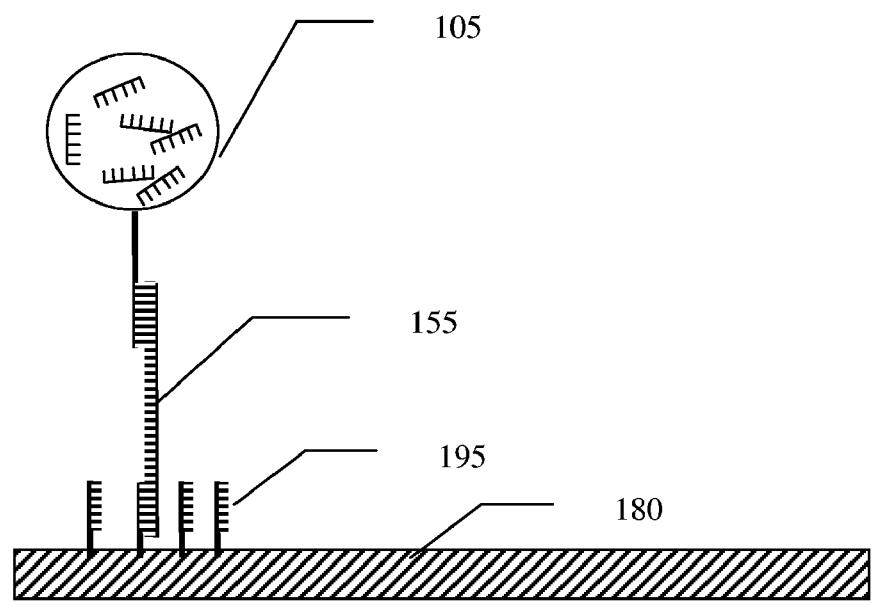
FIG. 5 illustrates embodiment of capturing of the analyte by the sensitized microcapsules and immobilized receptors.

The above description completes the analyte capture step according to the present invention. The same capture step is additionally illustrated by FIG. 5, with the sensitized microcapsule 105 attached to the surface 180 through a bridge formed by the captured analyte DNA or RNA 155. As a result of the capture step, the analyte is immobilized on the surface together with attached sensitized microcapsules.

After completing the capture step, the analyzed sample and unbound microcapsules are removed, preferably by a washing step, so that only the captured analyte with attached sensitized microcapsules remain immobilized on the surface.

Figure 6:
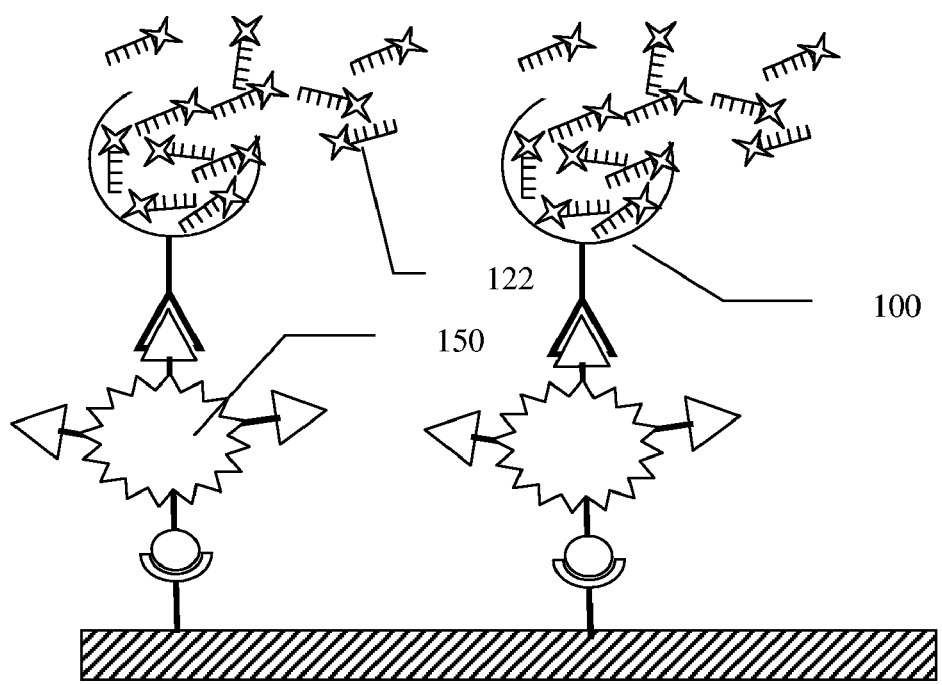
FIG. 6 illustrates disrupting of the sensitized microcapsules and release of oligomarkers.

Referring now to FIG. 6, the next step of the assay according to present invention is the step of disrupting of the immobilized sensitized microcapsules and releasing the oligomarkers. The microcapsules are disrupted by chemical, enzymatic, or physical-chemical means, including effects of pH, surfactant, temperature, or action of an enzyme. The preferred method is lysis by changing the pH of the solution or by adding a surfactant to the solution. The methods of disrupting of microcapsules are known to these skilled in the art.

As illustrated in FIG. 6, after disrupting of the sensitized microcapsules 100, the oligomarkers 122 are released. The oligomarkers are shown with a tag facilitating their detection and quantification. The amplification of the assay is a function of how many of the oligomarkers are released per each immunospecific or hybridization reaction binding act. Since oligomarkers are relatively small, a large number of these markers can fit into one sensitized microcapsule. If 1,000 oligomarkers can fit into a sensitized microcapsule, the assay amplification factor is 1,000. If 10,000 oligomarkers can fit into a sensitized microcapsule, the assay amplification factor is 10,000.

Figure 7:
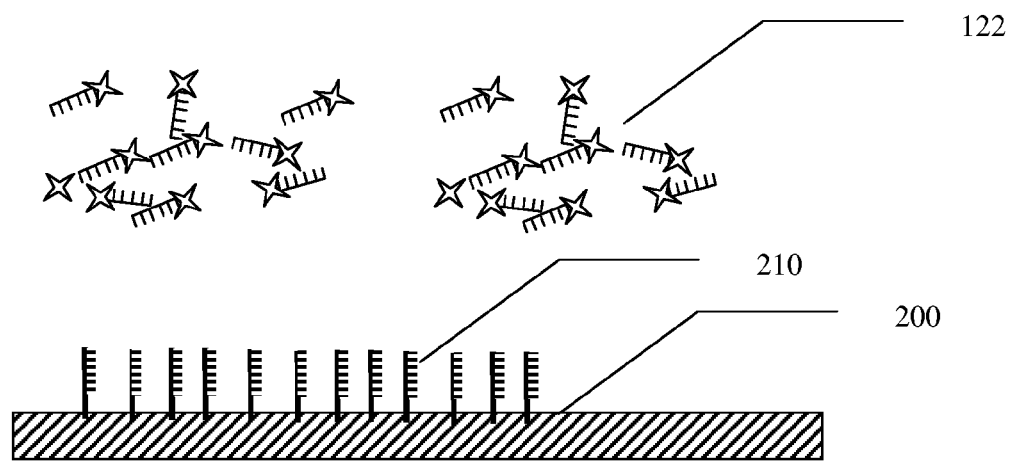
FIG. 7 illustrates quantitative capture and measurement of the oligomarkers released from disrupted or lysed microcapsules.

Referring now to FIG. 7, the next step of the assay is quantitative capture and measurement of the oligomarkers released from disrupted or lysed microcapsules. The oligomarkers can be captured and measured by a number of methods readily available to a skilled artisan as known and described in the art. For example, the oligomarkers 122 are brought into contact with complementary fragments of single strand DNA or RNA 210 immobilized on an inert surface 200.

Figure 8:
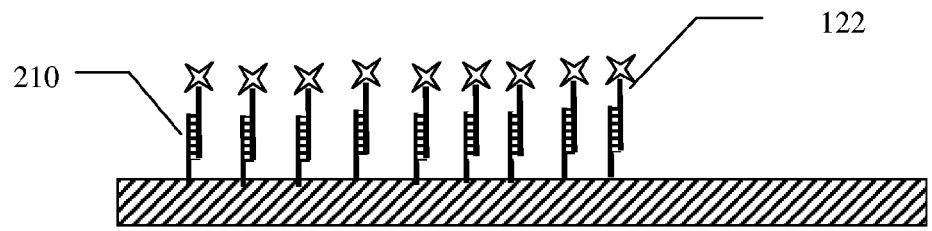
FIG. 8 illustrates capturing oligomarkers by hybridizing to immobilized complementary capture fragments of DNA or RNA.

Referring now to FIG. 8, the oligomarkers 122 are captured by hybridizing to immobilized complementary capture fragments of DNA or RNA 210.

The captured oligomarkers can now be quantified and detected by readily available devices, including by optical means by measuring fluorescence, the intensity of a dye, or the reflectivity of quantum dots; electrochemically utilizing an interdigitated electrode; utilizing electrochemiluminescence; using surface plasmon resonance techniques; using quartz microbalance or microcantilever techniques; and other techniques known in the art.

Yet another method of capturing and measuring the oligomarkers according to the present invention is by using DNA arrays and similar devices, for example DNA array devices manufactured by Affymetrix. In this embodiment, the oligomarkers are captured on a DNA array containing complementary DNA sequences and quantified as known in the art. Other methods of detecting the oligomarkers, including detection of tag-free markets, are piezoelectric, surface plasmon resonance, and colorimetry. An appropriate dye, such as SYBR green, to detect double strand DNA molecules formed by oligomarkers and complementary immobilized DNA fragments, can also be employed. Such methods are known to these skilled in the art and are readily available.

The following description will in more detail describe the multiplexing aspect of the amplified assay of the present invention.

Figure 9:
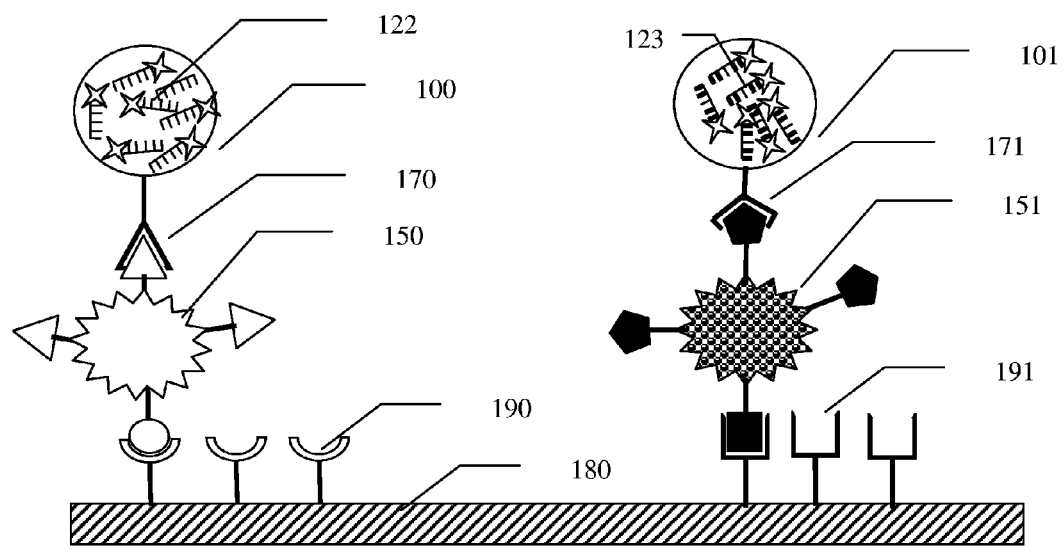
FIG. 9 illustrates the multiplexing aspect of the bioassay according to present invention, wherein there are at least two different types of sensitized microcapsules containing different oligomarkers.

Referring now to FIG. 9, the amplified multiplexing assay is performed as follows. There are at least two different types of sensitized microcapsules 100 and 101, containing oligomarkers 122 and 123 with different nucleotide sequences. In this embodiment, and for illustration only, the oligomarker 122 is a 20-mer oligonucleotide CTCTCTCTCTCTCTCTCTCT (SEQ ID NO: 1) with a tag, and oligomarker 123 is a 20-mer oligonucleotide TTTTTTTTTTTTTTTTTTTT (SEQ ID NO: 2) with a tag.

Each of the sensitized microcapsules 100 and 101 is sensitized to a different analyte utilizing receptor groups 170 and 171, such as immunospecific receptor groups. The sensitized microcapsules are brought into contact with the analyzed sample potentially containing at least two different analytes 150 and 151 and surface immobilized receptor groups 190 and 191 specific to each analyte.

The analytes, if present in the analyzed sample, are then captured by the sensitized microcapsules and surface immobilized receptors. The non-captured analyte and non-captured sensitized microcapsules are removed form the reaction area, preferably by a simple washing step.

Figure 10:
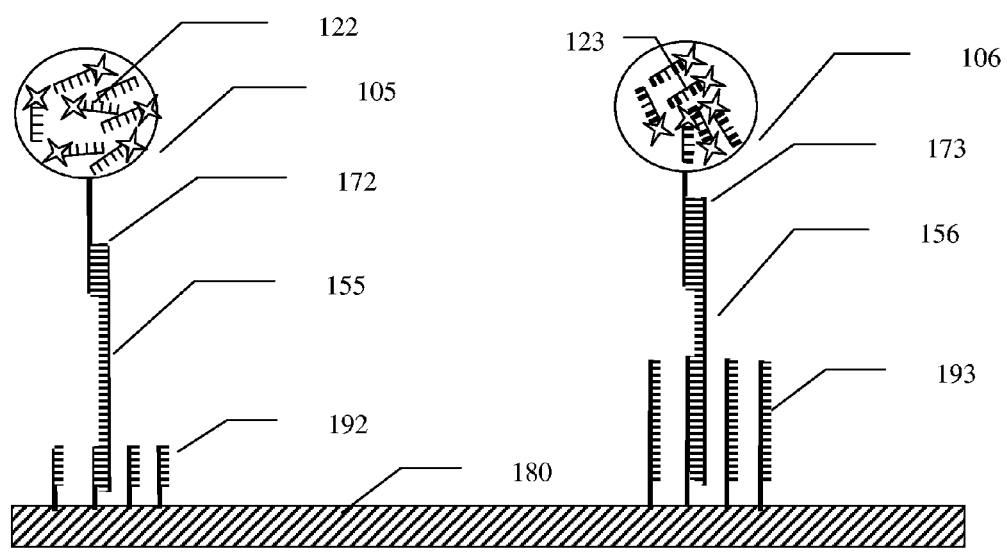
FIG. 10 illustrates embodiment of the amplified multiplexing assay, wherein receptor groups are single strand DNA or RNA capture molecules binding the analyte via hybridization.

Referring now to FIG. 10, another embodiment of the present amplified multiplexing assay is demonstrated whereas immobilized receptor groups 192 and 193 utilized in the assay are single strand DNA or RNA capture molecules binding the analyte 155 and 156 via hybridization. The sensitized microcapsules 105 and 106 are in turn being captured by the analyte through receptors 172 and 173, similar to above FIGS. 3 and 5.

Figure 11:
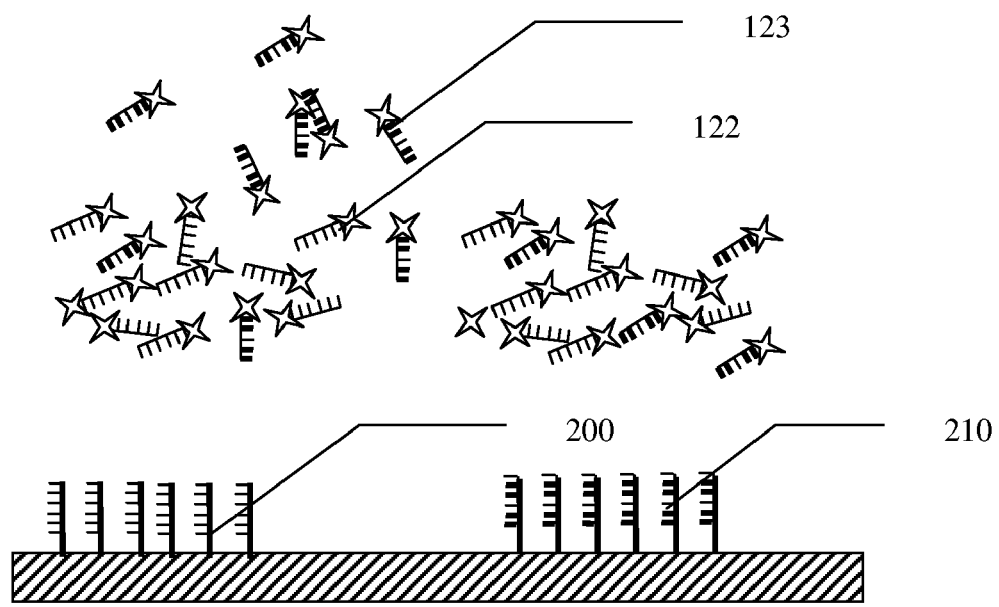
FIG. 11 illustrates disruption of immobilized sensitized microcapsules release of the oligomarkers which are then brought into contact with spatially separated immobilized single stranded arrays of complementary DNA or RNA fragments.

Referring now to FIG. 11, all immobilized microcapsules shown in FIGS. 9 and 10 are disrupted, for example by lysis, and the unique oligomarkers 122 and 123 contained in each type of the microcapsule are released and brought into contact with spatially separated immobilized single stranded arrays of complementary DNA or RNA fragments 200 and 210.

Figure 12:
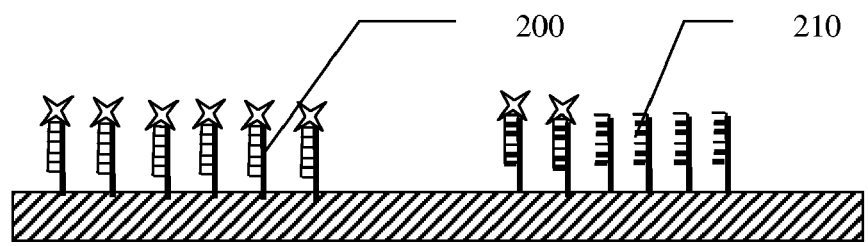
FIG. 12 illustrates how oligomarkers hybridize to the immobilized complementary single strand DNA or RNA receptors.

Referring now to FIG. 12, the oligomarkers hybridize to the immobilized complementary single strand DNA or RNA receptors 200 and 210. The spatial separation of the areas where the oligomarkers are immobilized permits to readily quantify the oligomarkers by any of the oligomarkers measurement techniques known in the art, as described above.

Figure 13:
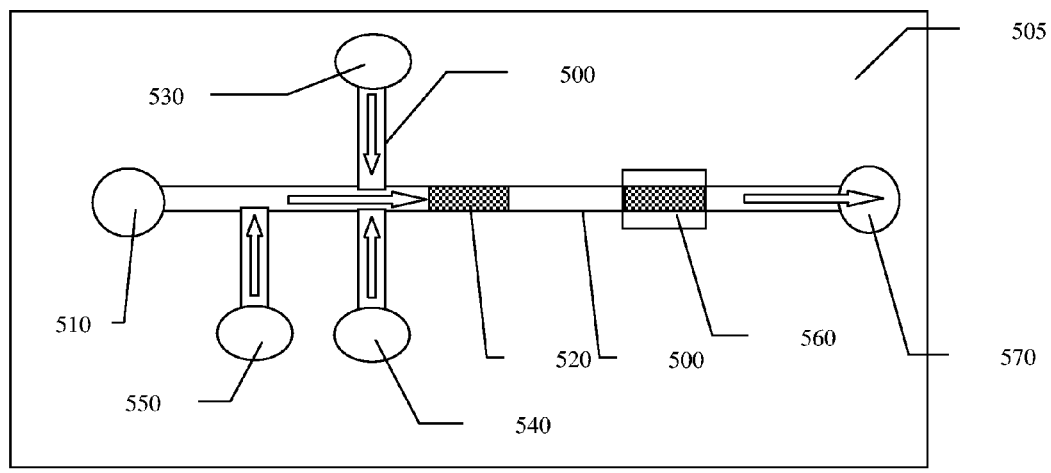
FIG. 13 illustrates a schematic diagram of a planar microfluidic device.

One embodiment for the implementation of the assay according to present invention is a planar microfluidic device. Methods of building such devices are readily available to these skilled in the art. Referring now to FIG. 13, a schematic diagram of the microfluidic device is shown. Channels 500 formed in the planar microfluidic device 505 enable movement of analyte samples and reagent fluids along the device as shown by arrows. The analyzed sample is introduced through a port 510 and moves in the direction of capture area 520. The sensitized microcapsules reservoir 530 provides sensitized microcapsules which are moving through a channel and also enter the capture area 520. The capture reactions in the capture area 520 were detailed above, specifically in FIGS. 4, 5, 9, and 10.

The reservoir 550 provides a washing buffer which removes all non-captured analyte and non-captured sensitized microcapsules, which are washed away and removed into the disposal reservoir 570. The lysing buffer reservoir 540 then supplies the lysing solution which disrupts the captured sensitized microcapsules in the capture area 520, resulting in the release of oligomarkers. The lysing process occurring in the capture area 520 was illustrated above, specifically in FIG. 6.

The oligomarkers released by lysing of the sensitized microcapsules continue moving through the channel towards the hybridization and measurement area 560. As it was illustrated in the FIGS. 7, 8, 11, and 12, the oligomarkers are bound through the hybridization process to immobilized complementary single stranded DNA or RNA.

Figure 14:
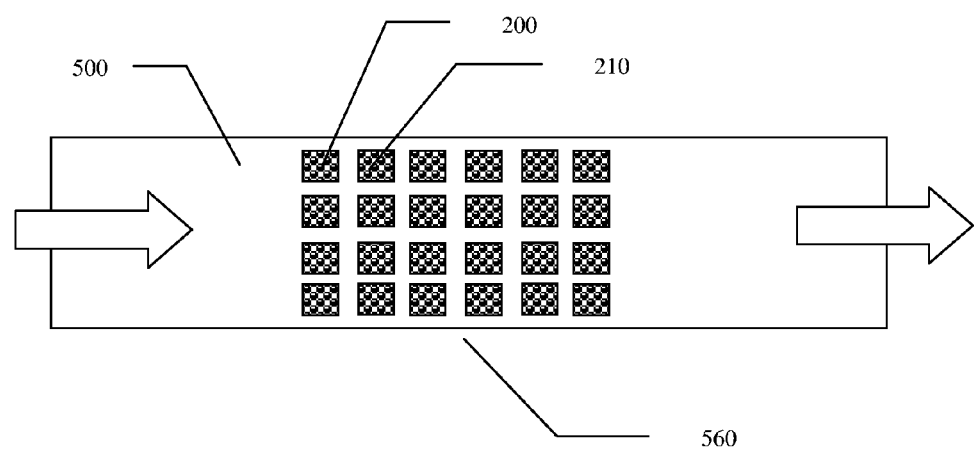
FIG. 14 illustrates hybridization and measurement area of the microfluidic device.

Referring now to FIG. 14, the hybridization and measurement area 560 of FIG. 13 is shown in more detail. A number of spatially separated areas 200, 210, etc. for hybridizing different oligomarkers is shown, each corresponding to a unique oligomarker sequence which in turn corresponds to a specific analyte. Following the illustration of FIG. 12, area 600 in FIG. 14 will capture specific oligomarkers 122, while area 210 will capture specific oligomarkers 123.

The amount of the released and captured oligomarkers is directly proportional to the amount of captured analyte. Quantifiably detecting oligomarkers in each of the areas 200, 210, etc., is readily performed by techniques known in the art and described above.

Fluidic reservoirs 510, 530, 540, 550, and 570 of the microfluidic device can be reusable, while the capture area 520 and measurement area 560 can be adapted for single use only.

Figure 15:
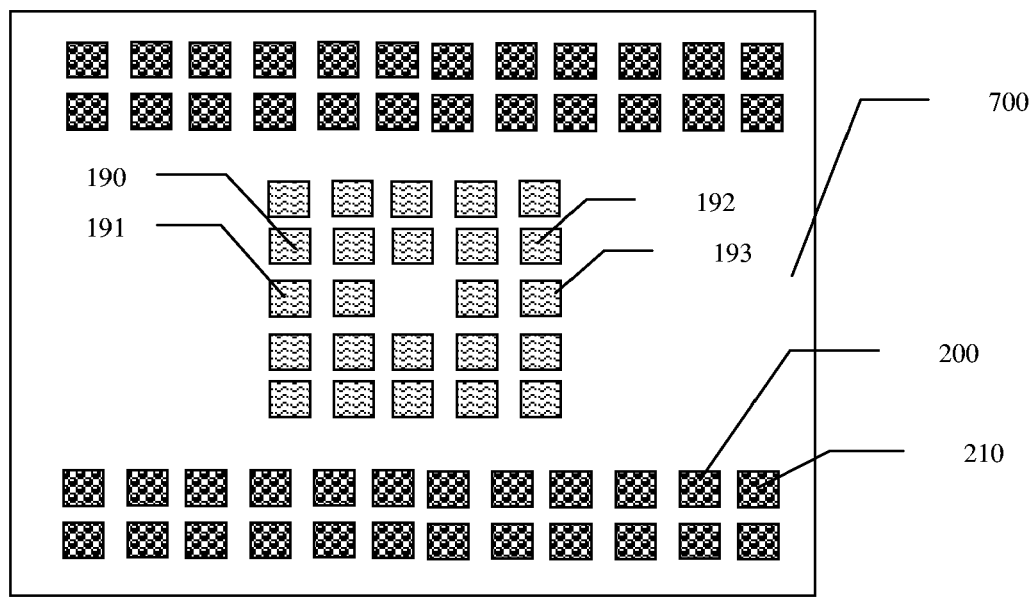
FIG. 15 illustrates embodiment of the bioassay in a well on a test plate.

Referring now to FIG. 15, another embodiment of the implementation of the assay according to present invention is in a well on a test plate. A well 700 has an analyte capture area where surface immobilized receptors 190, 191, 192, 193, etc., immunospecific or complementary to analytes of interest are situated. Elsewhere in the well are situated a number of spatially separated areas 200, 210, etc., for hybridizing different oligomarkers, each corresponding to a unique marker sequence, which in turn corresponds to a specific analyte.

The assay is performed by first sequentially or simultaneously introducing the analyzed biological fluid sample and sensitized microcapsules into the well and capturing the analytes present in the sample and corresponding sensitized microcapsules. After that the non-captured microcapsules and the rest of the sample are removed, preferably by washing.

In the next step, a buffer with a specific pH or containing a surfactant is introduced into the well and the captured sensitized microcapsules are lysed. The released oligomarkers are then hybridized in the spatially separated areas 200, 210, etc., and quantitatively measured by optical means. The preferred way of measuring and quantifying oligomarkers is by measuring fluorescence of fluorescent tags attached to oligomarkers.

Another embodiment of the implementation of the assay according to present invention comprises an assay performed in two wells on a test plate. The first well contains an analyte capture area where surface immobilized receptors for capturing analytes of interest are situated. The second well contains a number of spatially separated areas for hybridizing different oligomarkers, each corresponding to a unique oligomarker sequence which in turn corresponds to a specific analyte. The assay includes the steps of capturing the analytes and sensitized microcapsules and lysis of sensitized microcapsules in the first well, transfer of the released oligomarkers into the second well, binding or hybridization of the oligomarkers in the second well in the corresponding spatially separated areas, and quantifiable measurement of the hybridized oligomarkers in the second well.

The measurement is performed by detecting the tags conjugated to the oligomarkers, preferably by optical or electrochemical means, as known in the art.

The oligomarkers according to this invention can be made inexpensively in large quantities. Importantly, there are a high number of different and unique oligomarkers that can be made for this multiplexing assay by varying sequence, composition, and length of the oligonucleotide chain of the oligomarker, as well as type of the functional group or tag which makes the marker detectable. The preferred embodiment of this invention utilizes oligomarkers of the same length, for instance 20 base nucleotides long, with variable nucleotide sequences.

Figure 16:
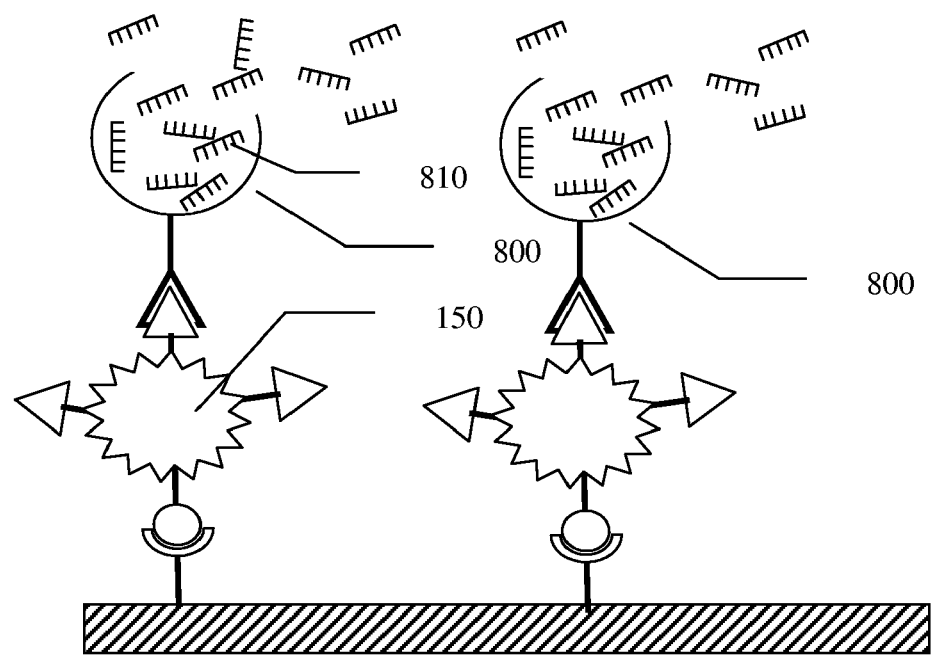
FIG. 16 illustrates embodiment of the present invention utilizing two types of sensitized microcapsules sequentially.

Referring now to FIG. 16, yet another embodiment of the present invention utilizes two types of sensitized microcapsules sequentially. The primary sensitized microcapsule 800 contains oligomarkers 810 without tags. After lysing of the primary sensitized microcapsule 800, as illustrated by FIG. 16, the oligomarkers are released.

Figure 17:
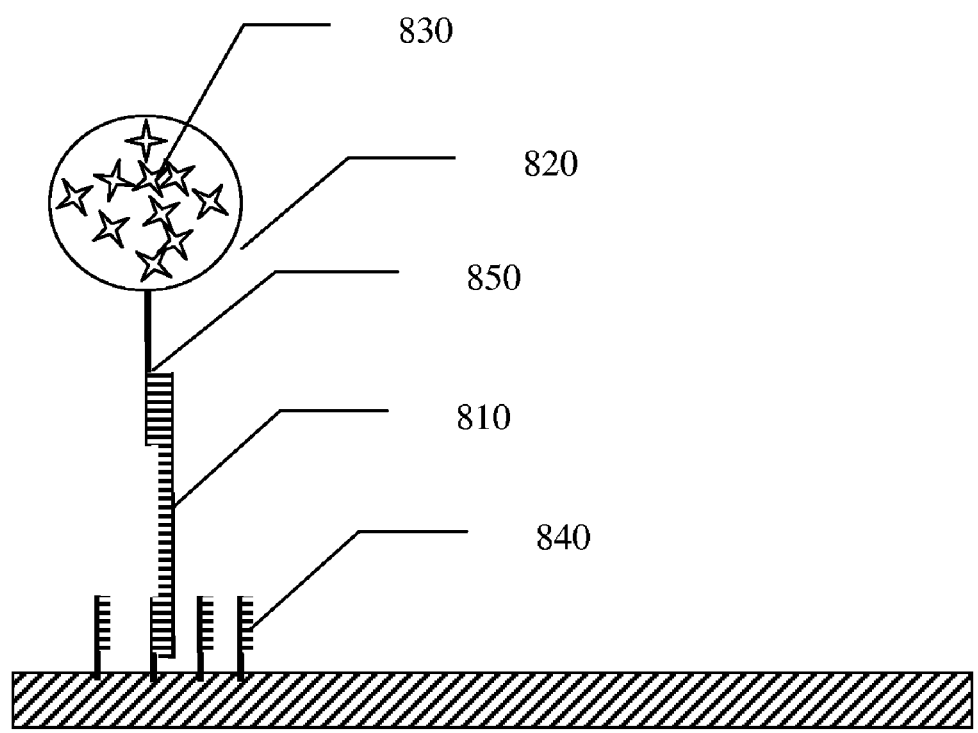
FIG. 17 illustrates how the oligomarkers released by a primary microcapsule are captured by surface immobilized complementary strand of DNA and a secondary microcapsule.

Referring now to FIG. 17, the oligomarkers 810, released by the primary sensitized microcapsule, are captured by the surface immobilized complementary strand of DNA 840 and a secondary sensitized microcapsule 820, which is sensitized with a single strand oligonucleotide 850 complementary to the oligomarkers released by the primary sensitized microcapsule. The secondary sensitized microcapsule, in turn, contains easily detectable tags 830 which are released by lysing the secondary sensitized microcapsule. The tags 830 are preferably fluorescent or electrochemical tags and are quantifiably measured, preferably by optical or electrochemical means.

In yet another embodiment of this invention, the secondary sensitized microcapsules according to FIG. 17 contain oligomarkers which are then captured via hybridization reaction and quantitatively measured.

The embodiment of the invention utilizing primary and secondary microcapsules enables additional significant amplification of the assay. If the primary sensitized microcapsule provides for amplification of 1000, and secondary sensitized microcapsule provides for amplification of 1000, then the resulting total assay amplification is 1,000,000.

Yet another embodiment of the present invention utilizes principles of the present invention for the biological tissue analysis or tissue typing, for example for detection of certain proteins, cancer cells, and the like on tissue samples. In this embodiment, the analytes are tissue components which are already immobilized on tissue samples.

The sensitized microcapsules are sensitized with receptors which are specific to certain tissue types or tissue proteins. Then the sensitized microcapsules are brought into contact with tissue samples and are captured by the tissue components and thus immobilized on the tissue.

After this capture step, all non-captured sensitized microcapsules are removed, preferably by a simple washing step. After the washing step, the captured or immobilized microcapsules are disrupted and the oligomarkers are released. The released oligomarkers are then measured and quantified as described above.

In yet another embodiment of the present invention, the principles of the invention are utilized to facilitate drug discovery. In this embodiment, prospective drug candidates, which can be small molecule chemical entities, peptides, proteins, and the like, are conjugated to microcapsules as receptors to form sensitized microcapsules. The successful binding of the sensitized microcapsules to the drug targets is then detected, with amplification, by disrupting microcapsules and measuring the released oligomarkers, as described above. Simultaneous testing of many drug candidates and on many targets is possible. The capture of the sensitized microcapsules is then used as indication of prospective drug candidates propensity for binding to targets.

Figure 18:
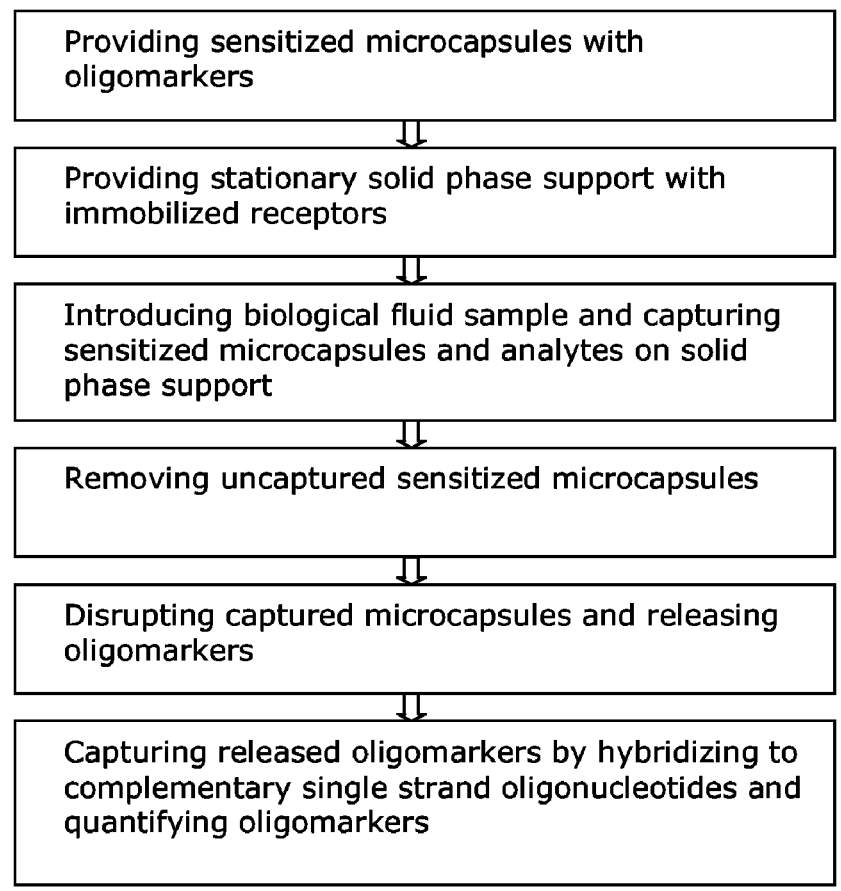
FIG. 18 presents a flow chart illustrating the sequence of the bioassay steps according to principles of the present invention.

Referring now to FIG. 18, a flow chart illustrating the principles of the present invention is presented. The main steps in carrying out the amplified multiplexing bioassay are outlined.

In carrying out the assay an aqueous medium will normally be employed. Other polar solvents may also be employed, usually oxygenated organic solvents of from 1 to 6, more usually from 1 to 4 carbon atoms, including alcohols, ethers and the like. Usually these cosolvents will be present in less than about 40 volume percent, more usually in less than about 20 volume percent.

The assay of this invention is carried out in an aqueous medium at a moderate pH, such as neutral pH, generally close to optimum assay sensitivity, without the need for separation of the assay components or products. The pH for the medium will usually be in the range of about 4 to 10, more usually in the range of about 5 to 9, and preferably in the range of about 5.5 to 8.5. The pH is chosen so as to maintain a significant level of specific binding by the receptor while optimizing signal producing efficiency. In some instances, a compromise will be made between these two considerations. Various buffers may be used to achieve the desired pH and to maintain the pH during the determination. Illustrative buffers include borate, phosphate, carbonate, Tris, Tris HCl, barbital and the like. The particular buffer employed is not critical to this invention but in individual assays, one buffer may be preferred over another.

From the foregoing description, one skilled in the art can easily ascertain the essential characteristics of this invention and, without departing from the spirit and scope thereof, can make various changes and modifications of the invention to adapt it to various usages and conditions. The present invention has been described in detail, including the preferred embodiments thereof. However, it will be appreciated that those skilled in the art, upon consideration of the present disclosure, may make modifications and improvements on this invention and still be within the scope and spirit of this invention as set forth in the following claims.

Incorporation by Reference. The contents of all references and patents cited herein are hereby incorporated by reference in their entirety.

What is claimed is:

1. A method for assaying a biological fluid sample potentially containing two or more analytes, which comprises the steps of:
   (a) providing a stationary solid phase support with immobilized receptors for binding thereto said analytes;
   (b) forming two or more different types of sensitized microcapsules comprising oligomarkers, each different type of said sensitized microcapsules having a surface membrane and an interior volume, said surface membrane of said each different type of said sensitized microcapsules having a receptor incorporated thereinto that specifically binds to a particular one of said analytes and said interior volume of said each different type of said sensitized microcapsules includes a unique oligomarker from said oligomarkers, each said unique oligomarker in said each different type of said sensitized microcapsules is different;
   (c) flowing said biological fluid sample over said solid phase support whereby said analytes bind to said immobilized receptors when said analytes are present in the biological fluid sample;
   (d) flowing said sensitized microcapsules over said solid phase support, whereby said sensitized microcapsules bind to said analytes bound to said immobilized receptors and forming complexes comprising said sensitized microcapsules, said analytes and said immobilized receptors when said analytes are present in the biological fluid sample;
   (e) disrupting said sensitized microcapsules on said complexes and releasing each said unique oligomarker from each different type of said sensitized microcapsules on said complexes when said analytes are present in the biological fluid sample; and
   (f) determining the presence of each of said analytes in said biological fluid sample by detecting each said unique oligomarker released from said each different type of said sensitized microcapsules on said complexes.

2. The method according to claim 1, wherein the detection is carried out with a device comprising:
   means for immobilizing each said unique oligomarker released from said each different type of said sensitized microcapsules on said complexes in spatially separated locations; and
   means for detecting each said oligomarker released from said each different type of said sensitized microcapsules on said complexes immobilized in said spatially separated locations.

3. The method according to claim 2, wherein said means for immobilizing each said unique oligomarker released from said each different type of said sensitized microcapsules on said complexes comprises an array of immobilized oligonucleotides complementary to said oligomarkers, wherein each said oligomarker released from said each different type of said sensitized microcapsules on said complexes is brought into contact with said array and hybridizes with said immobilized oligonucleotides.

4. The method according to claim 1, wherein said analytes are antigens or antibodies or cytokines or chemokines or enzymes or drugs or proteins or biomarkers or DNAs or RNAs.

5. The method according to claim 1, wherein said unique oligomarker is an oligonucleotide molecule alone or an oligonucleotide molecule conjugated to a fluorophore tag or an oligonucleotide molecule conjugated to an electrochemical tag or an oligonucleotide molecule conjugated to a quantum dot tag or an oligonucleotide molecule conjugated to a dye tag.

6. The method according to claim 1, wherein said microcapsules are liposomes or polymer based microspheres.

7. The method according to claim 1, wherein steps (c) and (d) are performed simultaneously by mixing said biological fluid sample with said sensitized microcapsules and said solid phase support with said immobilized receptors, and further comprising removing unbound said sensitized microcapsules.

8. A method for assaying a biological tissue sample potentially containing two or more analytes, which comprises:
   providing two or more different microcapsules comprising oligomarkers, each of said microcapsules capable of specifically binding to one of said analytes and contains a unique oligomarker, and each said unique oligomarker in said each of said microcapsules is different;
   providing a solid surface with immobilized receptors for binding thereto said analytes;
   bringing said microcapsules into contact with said biological tissue sample and said solid surface, and capturing said microcapsules on said solid surface by binding said microcapsules to said analytes and forming immobilized microcapsules when said analytes are present in said biological tissue sample;
   disrupting said immobilized microcapsules and releasing said oligomarkers from said immobilized microcapsules when said analytes are present in said biological tissue sample; and
   determining the presence of each of said analytes in said biological tissue sample by detecting each of said oligomarkers released from said immobilized microcapsules, wherein the detection is carried out with a device comprising:
   means for immobilizing each of said oligomarkers released from said immobilized microcapsules in spatially separated locations; and
   means for detecting each of said oligomarkers released from said immobilized microcapsules and immobilized in said spatially separated locations.

9. The method according to claim 8, wherein said unique oligomarker is an oligonucleotide molecule alone or an oligonucleotide molecule conjugated to a fluorophore tag or an oligonucleotide molecule conjugated to an electrochemical tag or an oligonucleotide molecule conjugated to a quantum dot tag or an oligonucleotide molecule conjugated to a dye tag.

10. The method according to claim 8, wherein said microcapsules are liposomes or polymer based microspheres.

11. The method according to claim 8, wherein said means for immobilizing each of said oligomarkers released from said immobilized microcapsules comprises an array of immobilized oligonucleotides complementary to said oligomarkers, wherein said oligomarkers are brought into contact with said array and hybridize with said immobilized oligonucleotides.

12. A method for assaying a biological sample potentially containing at least one analyte, said method comprising:
providing a first microcapsule filled with first oligomarkers, said first microcapsule being capable of specifically binding to said analyte;
providing a second microcapsule filled with tags, said second microcapsule being capable of specifically binding to said first oligomarkers;
providing an immobilized binder of said analyte and an immobilized binder of said first oligomarkers;
mixing said biological sample with said first microcapsule and said immobilized binder of said analyte, and forming an immobilized first microcapsule when said analyte is present in the biological fluid sample;
disrupting said immobilized first microcapsule and releasing said first oligomarkers from the first microcapsule when said analyte is present in the biological fluid sample;
mixing said first oligomarkers released from said first microcapsule with said immobilized binder of said first oligomarkers and said second microcapsule, and forming an immobilized second microcapsule when said analyte is present in the biological fluid sample;
disrupting said immobilized second microcapsule and releasing said tags when said analyte is present in the biological fluid sample; and
determining the presence of said analyte in said biological sample by detecting said tags released from said second microcapsule.

13. The method according to claim 12, wherein said tags are electrochemically detectable species or colorimetrically detectable species or fluorescent species or second oligomarkers or oligonucleotide molecules or oligonucleotide molecules conjugated to a fluorophore tag or an electrochemical tag or a quantum dot tag or a dye tag.

14. The method according to claim 13, wherein said colorimetrically detectable species or said fluorescent species or said electrochemically detectable species is detected with a detector which detects colorimetric, fluorescent, or electrochemical species.

15. The method according to claim 12, wherein said tags in said second microcapsule are second oligomarkers and wherein said detecting said tags released from said second microcapsule is carried out with a detector which comprises a means for immobilizing said second oligomarkers and a means for detecting said second oligomarkers which are immobilized, wherein said means for immobilizing said second oligomarkers comprise an array having complementary oligonucleotides immobilized thereof, and said second oligomarkers are brought into contact with said array and hybridize with said complementary oligonucleotides.

16. The method according to claim 12, wherein said analyte is an antigen or an antibody or a cytokine or a chemokine or an enzyme or a drug or a protein or a biomarker or a DNA or an RNA.

17. The method according to claim 12, wherein said first and second microcapsules are liposomes or polymer based microspheres.

* * * * *